United States Patent [19]

Kleiner et al.

[11] 4,426,336
[45] Jan. 17, 1984

[54] PROCESS FOR THE PREPARATION OF VINYLPHOSPHONIC ACID DERIVATIVES AND THE USE THEREOF

[75] Inventors: Hans-Jerg Kleiner, Kronberg; Walter Dürsch, Königstein, both of Fed. Rep. of Germany

[73] Assignee: Hoechst Aktiengesellschaft, Fed. Rep. of Germany

[21] Appl. No.: 297,736

[22] Filed: Aug. 31, 1981

[30] Foreign Application Priority Data

Sep. 6, 1980 [DE] Fed. Rep. of Germany ....... 3033615

[51] Int. Cl.³ .............................. C07F 9/30; C07F 9/32
[52] U.S. Cl. .............................. 260/986; 260/507.4 R; 260/928; 260/936; 260/982
[58] Field of Search ................ 260/982, 928, 502.4 R, 260/936, 986

[56] References Cited

U.S. PATENT DOCUMENTS

| | | | |
|---|---|---|---|
| 2,959,609 | 11/1960 | Leupold et al. | 260/986 |
| 3,035,096 | 5/1962 | Cooper | 260/986 |
| 3,548,040 | 12/1970 | Sorstokke et al. | 260/986 |
| 3,641,202 | 2/1972 | Biranowski et al. | 260/928 |
| 3,822,327 | 7/1974 | Weil | 260/928 |
| 3,959,414 | 5/1976 | Shim et al. | 260/928 |

FOREIGN PATENT DOCUMENTS 3014737 10/1981 Fed. Rep. of Germany .

Primary Examiner—Anton H. Sutto
Attorney, Agent, or Firm—Connolly and Hutz

[57] ABSTRACT

A process for the preparation of vinylphosphonic acid derivatives by heating 2-chloroethanephosphonic acid derivatives which contain 2-chloroethyl ester groups to temperatures of from 150° to 230° C.

8 Claims, No Drawings

PROCESS FOR THE PREPARATION OF VINYLPHOSPHONIC ACID DERIVATIVES AND THE USE THEREOF

Vinylphosphonic acid diesters can be prepared, as is known, from 2-halogenoethanephosphonic acid diesters by cleavage of hydrogen halide with bases. A simple process for the preparation of vinylphosphonic acid derivatives from 2-halogenoethanephosphonic acid derivatives is desired.

It has now surprisingly been found that vinylphosphonic acid derivatives can be prepared in a simple and economical manner by heating 2-chloroethanephosphonic acid derivatives containing 2-chloroethyl ester groups to 150°–230° C., preferably 170°–215° C., 1,2-dichloroethane being split off. The elimination can be carried out, if appropriate, in the presence of acid or basic catalysts. Salts of hypophosphorus acid are also suitable as catalysts.

The 2-chloroethanephosphonic acid derivatives, which contain 2-chloroethyl ester groups and which serve as starting materials, are prepared by the known Arbusow rearrangement of tris-chloroethyl phosphite. Bis-2-chloroethyl 2-chloroethanephosphonate is obtained as the most important compound in this rearrangement. Furthermore, non-distillable so-called polycondensates of structures which are essentially unknown, among these also the compound of the formula

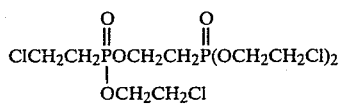

are also frequently obtained in the Arbusow rearrangement of tris-chloroethyl phosphite.

All these products can serve, alone or in mixtures with one another, as starting materials for the preparation of the vinylphosphonic acid derivatives. In addition, the mono-2-chloroethyl 2-chloroethane-phosphonate can also be used as a starting material.

However, the total reaction mixture of the Arbusow rearrangement, as produced in the rearrangement, that is to say, as a rule, the bis-2-chloroethyl 2-chloroethanephosphonate mixed with the non-distillable so-called polycondensates, is preferred as the starting material.

Numerous compounds are suitable as acid or basic catalysts. The following can be used as acid catalysts:

(A) Sulfuric acid, phosphoric acid, hydrochloric acid and hydrobromic acid;

(B) Halogen-containing carboxylic acids with a $P_{Ka}$ value <2.5, such as dichloroacetic acid, trichloroacetic acid and trifluoroacetic acid;

(C) Aromatic sulfonic acids with a $P_{Ka}$ value of <2.5, such as benzenesulfonic acid and p-toluenesulfonic acid;

(D) Preferably phosphonic acids having 2 to 18 carbon atoms, such as dimethylphosphinic acid, methylethylphosphinic acid, dioctylphosphinic acid, methylphenylphosphinic acid and diphenylphosphinic acid;

(E) Particularly preferably phosphonic acids having 1 to 18 carbon atoms and half-esters thereof having 1 to 4 carbon atoms in the alcohol radical, such as methanephosphonic acid, propanephosphonic acid, monomethyl propanephosphonate, octadecanephosphonic acid, 2-chloroethanephosphonic acid, mono-2-chloroethyl 2-chloroethanephosphonate, vinylphosphonic acid, mono-2-chloroethyl vinylphosphonate, monoethyl vinylphosphonate and benzenephosphonic acid.

(F) Pyrophosphonic acids or half-esters thereof, such as 2-chloroethanepyrophosphonic acid, benzenepyrophosphonic acid, vinylpyrophosphonic acid and mono-2-chloroethyl vinylpyrophosphonate, are also particularly preferred.

(G) The alkali metal salts, preferably sodium or potassium salts, of the acids mentioned under A to F are also suitable.

(H) The acid reaction mixtures which are formed in the process according to the invention are also very suitable.

The following can be used as basic catalysts:

(A) Tertiary aliphatic and aromatic amines and phosphines having 3 to 18 carbon atoms, such as trimethylamine, tripropylamine, tributylamine, triphenylamine, trimethylphosphine, triethylphosphine, tripropylphosphine, tributylphosphine, triphenylphosphine and tris-(p-dimethylaminophenyl)-phosphine, and the corresponding mixed amines, phosphines, phospholanes and phospholenes, such as dimethylethylamine, diethylbutylamine, N-dimethylaniline, 4-methyl-N-dimethylaniline, N-diethylaniline, N,N-tetramethylphenyldiamine or N-methylpyrrolidine; methyldiethylphosphine, dimethypropylphosphine, diethylbenzylphosphine, 1-methylphosphol-3-ene and 2-ethyl-3-methylphosphol-3-ene.

(B) Quaternary ammonium salts or phosphonium salts having 3 to 18 carbon atoms, such as tetramethylammonium chloride or bromide, tetraethylphosphonium chloride, trimethylbenzylammonium chloride, triethylbenzylammonium chloride, triethylbenzylammonium bromide, trimethylbenzylphosphonium chloride and triphenylethylphosphonium 2,4-diaminobenzenesulfonate;

(C) Heterocyclic compounds with an aromatic character, such as pyridine, 4-(dimethylamino)-pyridine and quinoline, and their various alkyl and dialkyl derivatives, preferably methyl or dimethyl derivatives, and imidazole, N-vinylimidazole, benzthiazole and 2-amino-6-ethoxybenzthiazole, and also phosphabenzoles;

(D) Acid amides, such as dimethylformamide, diethylformamide, N-dimethylacetamide, N-diethylpropionamide, N-methylbenzamide, N-methylpyrrolidone and N,N'-tetramethylterephthalic acid diamide, or ureas, such as tetramethylurea and trimethylphenylurea;

(E) Other nitrogen compounds or phosphorus compounds with an N atom or P atom which has a valency higher than 3, such as pyridine N-oxide, trimethylphosphine oxide, tributylphosphine oxide, trihexylphosphine oxide, triphenylphosphine oxide, trihexylphosphine oxide, trimethylphosphine oxide, dimethylphenylphosphine oxide, dimethylphenylphosphine sulfide, dimethylchloromethylphosphine oxide, dimethyleicosylphosphine oxide, dimethyldodecylphosphine oxide, dimethylphosphine oxide, dimethylpyrrolidinyl-1-methylphosphine oxide, triphenylphosphine dichloride, dimethyldodecylphosphine sulfide, triphenylphosphinimine, dimethylchloromethylphosphine dichloride, N-2-dimethylphosphinylethyl-methyl-acetamide and N-2-dimethylphosphinyl-ethylmethyl-amine, and phospholene oxides, such as 1-methylphosphol-1ene oxide and 1-ethyl-3-methylphosphol-1-ene oxide;

(F) Amides of phosphinus and phosphonus acids and of phosphinic acids and phosphonic acids and their thioanalogs, such as ethanephosphonic acid bis-diethylamide, methanebutanephosphinus acid dimethylamide and diethylphosphinus acid isobutylamide, and also triamides of phosphoric acid and thiophosphoric acid, such as hexamethylphosphoric acid triamide.

(G) Alkali metal carbonates, preferably sodium carbonate and potassium carbonate, alkali metal hydroxides, preferably sodium hydroxide and potassium hydroxide, and alkali metal alcoholates, preferably sodium methylate.

The salts of hypophosphorus acid, for example sodium hypophosphite and potassium hypophosphite, are also suitable catalysts. These catalysts are also particularly preferred as additives which largely prevent a dark discoloration of the reaction material.

The catalysts are employed in quantities of from 0.01 to 10, preferably 0.1 to 5, % by weight. If the acid reaction mixtures which have already been obtained are used, relatively large quantities of from 10 to 50% by weight can also be employed.

The process is carried out, in general, by heating the starting materials to the reaction temperature. The elimination of the 1,2-dichloroethane then begins, accompanied as a rule by the simultaneous cleavage of relatively small quantities of hydrogen chloride. The 1,2-dichloroethane which splits off distils off, as a rule, under normal pressure, if appropriate with the aid of an inert gas stream. Nitrogen is particularly suitable as the inert gas. In an individual case, it can be advantageous, especially at the end of the reaction, to distil off the 1,2-dichloroethane in vacuo. The elimination of the 1,2-dichloroethane has ended after about 5 to about 20 hours. In the case of complete elimination of the 1,2-dichloroethane, the end product is then largely chlorine-free or poor in chlorine. However, it is not advantageous to carry out the elimination of the 1,2-dichloroethane until the end product is completely chlorine-free, but only to a content of about 1 to about 10%, preferably 5 to 8%. This chlorine is preferably in the form of chloroethyl groups. End products which are largely chlorine-free are mostly less suitable for further processing, since they frequently have a dark discoloration and already tend to decompose at the high reaction temperatures.

The reaction temperatures are 150° to 230° C., preferably 170° to 215° C. Higher temperatures are possible, but are of no advantage. There is a danger of decomposition, and also of polymerization.

If the catalysts which have previously been mentioned are used, the reaction can be carried out at somewhat lower temperatures than is possible without catalysts. Furthermore, the catalysts frequently favorably affect the color of the end product. The process can also be designed as a continuous process. The addition of polymerization inhibitors, such as, for example, hydroquinone, hydroquinone monomethyl ether or phenothiazine, can be advantageous.

The reaction products comprise mixtures of vinylphosphonic acid derivatives, the type and the quantity of the individual constituent being unknown. In the ideal case, with bis-2-chloroethyl 2-chloroethanephosphonate as the starting material, a mixture of the compounds of the formulae

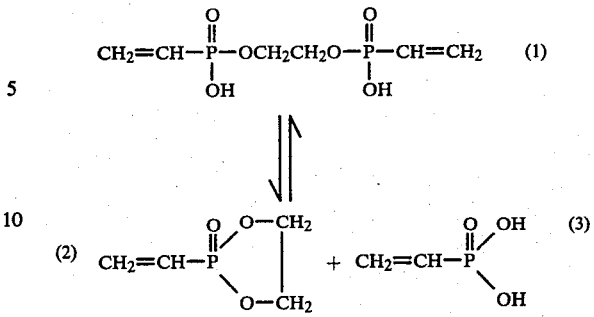

is obtained. The two compounds (2) and (3) exist in equilibrium with the compound (1). In addition, the reaction mixture also contains vinylpyrophosphonic acid or derivatives thereof. However, independently of the type of starting compounds used, all the individual compounds present in the reaction mixture contain vinylphosphonic acid groups and, depending on the chlorine content, a certain number of chloroethyl groups. The vinylphosphonic acid derivatives according to the invention are water-soluble, even with the chlorine content of 1 to 10% indicated.

The mixtures thus obtained, of various vinylphosphonic acid derivatives, can be used directly without isolation of individual compounds, namely as valuable intermediates for the preparation of substances for flame-retarding for textile materials. For this purpose, the vinylphosphonic acid derivatives are first reacted with ethylene oxide. These oxethylated products are then polymerized, via the vinyl groups, onto the material to be finished, whereby an excellent flame-retarding effect is obtained.

EXAMPLE 1

120 g of bis-2-chloroethyl 2-chloroethanephosphonate are heated to 208° to 215° C., whilst stirring. 59 g of 1,2-dichloroethane are distilled off during the course of 5 hours. 59 g of vinylphosphonic acid derivatives remain.

(Acid number: 371, iodine number: 144; 22.7% of P, 7.6% of Cl).

EXAMPLE 2

120 g of non-distillable polycondensates, which are produced in the Arbusow rearrangement of tris-chloroethyl phosphite and which have a proportion of 32% of 2-chloroethanephosphonic acid 2-chloroethyl ester 2-(bis-[2-chloroethoxy]-phosphono)-ethyl ester, are heated to 200° C., whilst stirring. 41 g of 1,2-dichloroethane with a content of 0.8% of hydrogen chloride are split off in the course of 6 hours. 76 g of vinylphosphonic acid derivatives are obtained.

(Acid number: 338, iodine number: 148).

EXAMPLE 3

240 g of a mixture from the Arbusow rearrangement of tris-chloroethyl phosphite, which contains 50% of bis-2-chloroethyl 2-chloroethanephosphonate and 16% of 2-chloroethanephosphonic acid 2-chloroethyl ester 2-(bis-[2-chloroethoxyl]-phosphono)-ethyl ester, are heated to 190° to 212° C., whilst stirring. 108 g of 1,2-dichloroethane are split off during the course of 7.5 hours. A vacuum from a water jet is applied for a further hour, a further 10 g of 1,2-dichloroethane collecting in a cold trap upstream from the pump. 117 g of vinylphosphonic acid derivatives remain.

(Acid number: 415, iodine, number 141; 3.1% of chlorine).

EXAMPLE 4

2.4 g of sodium hypophosphite monohydrate are added to 800 g of the mixture from the Arbusow rearrangement, as used in Example 3, and the mixture is heated to 160° C., whilst flushing with nitrogen and stirring. The cleavage of 1,2-dichloroethane begins. The temperature is now gradually increased to approximately 180° C. and 1,100 g of the same Arbusow mixture, mixed with 3.3 g of sodium hypophosphite monohydrate, are uniformly added dropwise to the mixture, whilst 1,2-dichloroethane distils off. In the course of this process, the temperature is increased to 200° C. after 7.5 hours. The mixture is cooled after 12 hours, whilst flushing with nitrogen. 821 g of 1,2-dichloroethane with a content of 0.3% of hydrogen chloride are obtained in the receiving flask. A further 25 g of 1,2-dichloroethane are collected in a cold trap downstream from the receiving flask. 1,035 g of vinylphosphonic acid derivatives remain.

(Acid number: 414, iodine number 126; 22.8% of phosphorus, 8.9% of chlorine).

EXAMPLE 5

135 g of bis-2-chloroethyl 2-chloroethanephosphonate and 4 g of phosphoric acid tris-dimethylamide are heated to 185° to 190° C. for 6 hours, whilst stirring. 66 g of 1,2-dichloroethane distil off into the receiving flask during this process. A vacuum of 47 mbars is then applied for 6 hours. A further 6 g of 1,2-dichloroethane condense in a cold trap downstream from the receiving flask. 65.5 g of vinylphosphonic acid derivatives remain.

(Acid number: 374, iodine number: 121; 24.1% of phosphorus, 1.5% of chlorine).

EXAMPLE 6

85.3 g of non-distillable polycondensates, as used in Example 2, and 1.7 g of 4-dimethylaminopyridine are heated to 190° C. for 10 hours, whilst stirring. 32 g of 1,2-dichloroethane distil off in this process. 53 g of vinylphosphonic acid derivatives remain.

(Acid number: 362, iodine number: 140; 23.2% of phosphorus; 5.6% of chlorine).

EXAMPLE 7

85.3 g of non-distillable polycondensates, as used in Example 2, and 3.4 g of 1-methyl-1-oxo-$\Delta^3$-phospholene are heated to 180° to 190° C. for 13 hours, whilst stirring. 29.5 g of 1,2-dichloroethane distil off. 53 g of vinylphosphonic acid derivatives remain.

(Acid number: 383, iodine number: 133; 24.5% of phosphorus, 4.7% of chlorine).

EXAMPLE 8

85.3 g of non-distillable polycondensates, as used in Example 2, and 1.7 g of triphenylphosphine are heated to 190° C., whilst stirring. 29.5 g of 1,2-dichloroethane are distilled off during the course of 9 hours. By applying a vacuum of 67 mbars, a further 5.5 g of 1,2-dichloroethane are collected in a cold trap downstream from the receiving flask. 51 g of vinylphosphonic acid derivatives remain.

(Acid number: 371, iodine number: 133; 24.3% of phosphorus, 4.1% of chlorine).

EXAMPLE 9

85.3 g of non-distillable polycondensates, as used in Example 2, and 1.7 g of 1,4-diazabicyclo[2,2,2]-octane ("Dabco") are heated to 185° to 190° C., whilst stirring. 32 g of 1,2-dichloroethane distil off during the course of 5 hours. 54 g of vinylphosphonic acid derivatives are obtained.

(Acid number: 368, iodine number: 124; 23.1% of phosphorus, 5.1% of chlorine).

EXAMPLE 10

269.5 g of the mixture from the Arbusow rearrangement, as used in Example 3, and 10 g of vinylphosphonic acid are heated to 195° C., whilst stirring. 1,2-Dichloroethane begins to distil off after one hour. When approximately 50 g of 1,2-dichloroethane have distilled off, a further 1,347.5 g of starting material are metered into the mixture during the course of 3 hours. The mixture is then heated for a further 6 hours at 195° C., whilst stirring. Thereafter, a vacuum of 67 mbars is applied at this temperature. A total of 678 g of 1,2-dichloroethane is collected in the receiving flask, and 128 g of 1,2-dichloroethane in a cold trap downstream from the receiving flask. 804 g of vinylphosphonic acid derivatives remain.

(Acid number: 384, iodine number: 146; 24.5% of phosphorus, 4.4% of chlorine).

EXAMPLE 11

202 g of the mixture from the Arbusow rearrangement, as used in Example 3, and 1 g of anhydrous sodium carbonate are heated to 190° C., whilst stirring. 84 g of 1,2-dichloroethane distil off during the course of 8 hours. 117 g of vinylphosphonic acid derivatives remain.

(Acid number: 310, iodine number: 136; 21.3% of phosphorus, 11.1% of chlorine).

EXAMPLE 12

202 g of the Arbusow rearrangement product, as used in Example 3, and 1 g of sodium chloride are heated to 190° C., whilst stirring. 87.5 g of 1,2-dichloroethane distil off during the course of 9 hours. 114 g of vinylphosphonic acid derivatives are obtained.

(Acid number: 325, iodine number: 144; 22.2% of phosphorus, 9.9% of chlorine).

EXAMPLE 13

202 g of the mixture from the Arbusow rearrangement, as used in Example 3, and 1 g of monosodium ethanephosphonate are heated to 190° C., whilst stirring. 91.5 g of 1,2-dichloroethane distil off during the course of 12 hours. 110 g of vinylphosphonic acid derivatives remain.

(Acid number: 350, iodine number: 128; 23.0% of phosphorus, 8.4% of chlorine).

We claim:
1. A process for the preparation of vinylphosphonic acid derivatives from a 2-chloroethane phosphonic acid derivative having at least one 2-chloroethylester group, said process comprising:
heating a reaction medium comprising at least one 2-chloroethane phosphonic acid derivative containing at least one 2-chloroethyl ester group to a temperature of from 150° to 230° C. and splitting off 1,2-dichloroethane from said 2-chloroethanephosphonic acid derivative, thereby obtaining at least one vinyl phosphonic acid derivative having an unpolymerized vinyl group.

2. A process according to claim 1, wherein the 2-chloroethanephosphonic acid derivative is the total reaction mixture obtained from an Arbusow rearrangement.

3. A process according to claim 1, wherein the resulting derivative contains about 1–10% chlorine, and the 1,2-dichloroethane is eliminated from the reaction medium as the heating step proceeds.

4. A process according to claim 3, wherein the 1,2-dichloroethane is eliminated from the reaction medium by distillation, and cleavage of hydrogen chloride occurs, if at all, only to a relatively small extent during the elimination of the 1,2-dichloroethane.

5. A process according to claim 1, wherein the reaction occurring during the heating step includes the conversion of a 2-chloroethyl ester group to a hydroxyl group and the conversion of a 2-chloroethane phosphonic acid group to a vinylphosphonic acid group, with splitting off of 1,2-dichloroethane.

6. A process for the preparation of vinylphosphonic acid derivatives, which comprises heating 2-chloroethanephosphonic acid derivatives which contain 2-chloroethyl ester groups to temperatures of from 150° to 230° C.

7. A process as claimed in claim 6, wherein the reaction is carried out in the presence of acid or basic catalysts.

8. A process as claimed in claim 6, wherein the reaction is carried out in the presence of salts of hypophosphoric acid.

* * * * *